(12) United States Patent
Shou et al.

(10) Patent No.: US 7,250,395 B2
(45) Date of Patent: Jul. 31, 2007

(54) ANTAGONIST PEPTIDES TO VEGF RECEPTOR FLT-1

(75) Inventors: Chengchao Shou, Beijing (CN); Hetian Lei, Bejing (CN); Ping An, Beijing (CN); Jian Wu, Beijing (CN); Lin Meng, Beijing (CN); Xiaoying Liu, Beijing (CN)

(73) Assignee: Beijing Institute for Cancer Research (CN)

( * ) Notice: Subject to any disclaimer, the term of this patent is extended or adjusted under 35 U.S.C. 154(b) by 212 days.

(21) Appl. No.: 10/489,344

(22) PCT Filed: Sep. 12, 2001

(86) PCT No.: PCT/CN01/01393

§ 371 (c)(1),
(2), (4) Date: Oct. 28, 2004

(87) PCT Pub. No.: WO03/022874

PCT Pub. Date: Mar. 20, 2003

(65) Prior Publication Data

US 2005/0154187 A1 Jul. 14, 2005

(51) Int. Cl.
*A61K 38/10* (2006.01)
*A61K 38/16* (2006.01)

(52) U.S. Cl. ......................................................... 514/2

(58) Field of Classification Search ...................... None
See application file for complete search history.

(56) References Cited

U.S. PATENT DOCUMENTS 6,610,836 B1 * 8/2003 Breton et al. .............. 536/23.1

FOREIGN PATENT DOCUMENTS

| WO | WO 97/08313 | 3/1997 |
|---|---|---|
| WO | WO 01/72829 | 4/2001 |

OTHER PUBLICATIONS

Sutter et al. "Gene therapy for gastric cancer: is it promising?" World J Gastroenterol., 2006, 12, 380-7.*

Aslanidis et al. "Nucleotide sequences and operon structure of plasmid-borne genes mediating uptake and utilization of raffinose in *Escherichia coli*." Journal of Bacteriology, 1989, 171, 6753-63.*

Jekel et al. "Panulirus interruptus hemocyanin," Eur. J. Biochem., 1988, 178, 403-12.*

Liu et al. "Cancer gene therapy targeting angiogenesis: An updated review." World J. Gastroenterol., 2006, 12, 6941-8.*

Ginalski et al. "Practical lessons from protein structure prediction." Nuc. Ac. Res., 2005, 33, 1874-1891.*

Rudinger "Characteristic of the amino acids as components of a peptide hormone sequence." (Peptide Hormones(Ed. J.A. Parson). University Park Press. Baltimore, 1976, pp. 1-7.*

Pitt et al. "Single amino acid substitution mutants of Klebsiella pneumoniae singma54 defective in transcription" Nuc. Ac. Res., 2000, 28, 4419-4427.*

Bradley et al. "Limits of Cooperativity in a Structurally Modular Protein: Response of the Notch Ankyrin Domain to Analogous Alanine Subsitutions in Each Repeat" J. Mol. Biol., 2002, 324, 373-386.*

Flanagan et al. "Truncated staphyloccal nuclease is compact but disordered" Proc. Natl. Acad. Sci. USA, 1992, 89, 748-752.*

Sawai et al. "Impact of single-residue mutations on the structure and function of ovispirin/novispirin antimicrobial peptides" Prot. Engin., 2002, 15, 225-232.*

Schnog et al. "Sickle cell disease; a general overview" J. Med., 2004, 62, 364-374.*

* cited by examiner

*Primary Examiner*—Cecilia J. Tsang
*Assistant Examiner*—Christina Marchetti Bradley
(74) *Attorney, Agent, or Firm*—Connolly Bove Lodge & Hutz LLP (57) ABSTRACT

The present invention provides a polypeptide or a pharmacologically acceptable salt thereof comprising one or more, identical or different, amino acid sequences of A-W—H—X1-D-X2-X3-X4-W—W—X5-X6-X7-X8-B (the meaning of each symbol in the formula is defined in the description) and a pharmaceutical composition for treating an angiogenic disease such as a solid tumor comprising said polypeptide. The present invention also relates to a polynucleotide encoding the above-mentioned polypeptide and use of the polynucleotide in gene therapy.

4 Claims, 2 Drawing Sheets

Fig.1 Inhibition of binding of VEGF to sFlt-1 by fusion protein DHFR-F56

Fig.2 Peptide F56 has no effect on proliferation of endothelial cells promoted by VEGF Fig.5 Inhibition of tumor growth on tumor-bearing SCID mice by peptide F56

ANTAGONIST PEPTIDES TO VEGF RECEPTOR FLT-1

FIELD OF THE INVENTION

The present invention relates to peptides acting as antagonists to VEGF receptor Flt-1 and useful in the treatment of angiogenic diseases. The present invention also relates polynucleotides encoding the peptides, vectors and cells containing the polynucleotides, methods and pharmaceutical compositions for treating angiogenic diseases by using the peptides, polynucleotides, vectors or cells.

BACKGROUND OF THE INVENTION

Angiogenesis is essential for normal biological processes including reproduction, development and wound healing. Although angiogenesis is a highly regulated process in normal conditions, many diseases are caused by persistent disorders of angiogenesis. Theses diseases are called angiogenic diseases. That is, the disorders of angiogenesis can cause particular diseases directly, or exacerbate the existing diseases. For instance, the neovascularization in eye is the most common cause of blindness. In some existing diseases such as arthritis, new-developed capillaries invade the joint and destroy cartilage. In diabetes, new-developed capillaries invade vitreous, resulting in bleeding and blindness. Growth and metastasis of solid tumor depend on neovascularization which involves the degradation of the basement membrane of the starting blood vessel, the proliferation and migration of endothelial cells, and the development of new vessels (Folkman J. Angiogenesis in cancer, rheumatoid and other disease. Nature Med., 1995a, 1, 27-30) etc.

As a member of the family of platelet-derived growth factors, vascular endothelial growth factor (VEGF) is the most direct nitogen of vascular endothelial cells (Ferrara N., Molecular and biological properties of vascular endothelial growth factor. J. Mol. Med., 1999, 77:527-543). The activities of VEGF are mediated by binding to its receptors (VEGFR), and its biological effects are exhibited through endocellular signal transduction. The binding of VEGF to its receptor Flt-1 (fms-like tyrosine domain containing receptor) can result in endothelial cell migration, differentiation, and ultimately forming tubular structure (blood vessel rudiment). Flt-1 is an important target for inhibiting angiogenesis (Hanahan H., Signaling vascular morphogenesis and maintenance. Science, 1997, 277:48-50; Shinichi K. et al., Roles of two VEGF receptors, Flt-1 and KDR, in the VEGF effects in human vascular endothelial cells. Oncogene, 2000, 19: 2138-2146).

Some peptides acting as antagonists against VEGF binding to its receptor KDR are reported by Binetruy-Tournaire R. et al. in The EMBO Journal. 2000, 19(7): 1525-1533. It is said that they can inhibit the neovascularization induced by VEGF.

Due to the fact that the angiogenesis inhibitors clinically available are not satisfactory in terms of, among others, their severe system toxicity (Suramin) or weak activity of anti-angiogenesis (interferon, antiestrogen), therefore new angiogenesis inhibitors are needed.

SUMMARY OF THE INVENTION

The present invention provides a polypeptide having one or more amino acid sequences of the following formula (I), which may be identical or different, or a pharmaceutically acceptable salt thereof:

$$A-W-H-X1-D-X2-X3-X4-W-W-X5-X6-X7-X8-B \quad (I)$$

wherein:

A is 0 to 3 optionally protected naturally occurring amino acid residues;

X1-X5 independently represents a sectuence gap or an optionally protected naturally occurring amino acid residues;

X6 represents a sequence gap or an optionally protected naturally occurring hydrophobic amino acid residue;

X7 represents a sequence gap or an optionally protected naturally occurring amino acid residue;

X8 represents a sequence gap or an optionally protected naturally occurring hydrophobic amino acid residue;

B is 0 to 3 optionally protected naturally occurring amino acid residues;

W represents optionally protected tryptophan;

H represents optionally protected histidine;

D represents optionally protected aspartate.

The present invention also provides a pharmaceutical composition comprising one or more peptides of the present invention as described above and optionally a pharmaceutically acceptable carrier or excipient.

The present invention relates to a peptide of the present invention as a medicament, especially as a medicament for treating angiogenic diseases.

The present invention also relates to use of one or more peptides of the present invention as described above for the preparation of a medicament for treating angiogenic diseases.

The present invention also provides a method for treating a subject in need of anti-angiogenesis treatment, comprising administering to the subject a therapeutically effective amount of one or more peptides of the present invention as described above.

The present invention further relates to a nucleotide sequence encoding a peptide of the present invention as described above.

The present invention also relates to a plasmid or viral vector containing a nucleotide sequence of the present invention as described above.

The present invention also relates to a cell containing a nucleotide sequence or a vector of the invention as described above.

The present invention also provides a nucleotide sequence, vector or cell line of the present invention as a medicament.

The present invention also relates to a pharmaceutical composition for treating angiogenic diseases containing a nucleotide sequence, vector or cell line of the invention as described above.

The present invention further relates to use of a nucleotide sequence or vector of the present invention in preparing, from cells obtained from a subject, cells to be redelivered to said subject for treating angiogenic diseases.

The present invention relates to a method for treating angiogenic diseases, which comprises administering to a subject in need of such treatment a therapeutically effective amount of a nucleotide sequence, vector or cell of the present invention as described above.

DETAILED DESCRIPTION OF THE INVENTION

Based on the strategy of inhibiting angiogenesis by blocking VEGF from binding to its corresponding receptor Flt-1, the inventor used soluble Ftl-1 obtained by cloning and expression as target to screen phage peptide library. The inventor discovered and proved by in vivo and in vitro experiments that the peptides and fusion proteins containing the peptides as set forth below have anti-angiogenesis activity and can inhibit growth and metastasis of tumor and treat other angiogenic diseases.

A-W—H—X1-D-X2-X3-X4-W—W—X5-X6-X7-X8-B    (I)

wherein:

A is 0 to 3 optionally protected naturally occurring amino acid residues;

X1-X5 independently represent a sequence gap or optionally protected naturally occurring amino acid residues;

X6 represents a sequence gap or an optionally protected naturally occurring hydrophobic amino acid residue;

X7 represents a sequence gap or an optionally protected naturally occurring amino acid residue;

X8 represents a sequence gap or an optionally protected naturally occurring hydrophobic amino acid residue;

B is 0 to 3 optionally protected naturally occurring amino acid residues;

W represents optionally protected tryptophan;

H represents optionally protected histidine;

D represents optionally protected aspartate.

In a preferred embodiment, the peptides of the present invention are unprotected free peptides or pharmaceutically acceptable salts thereof.

In another preferred embodiment, the α amino group on N-terminal of the peptides of the present invention has an amino protective group, and/or the α carboxy group on C-terminal has a carboxylic protective group.

Preferably, in the above formula (I), X2 represents a sequence gap or Pro.

Preferably, in the above formula (I), X5 is a polar amino acid residue.

Preferably, in the above formula (I), X7 is a hydrophobic amino acid residue.

In a preferred embodiment, the polypeptide of the present invention contains one amino acid sequence of formula (I). In this embodiment, more preferably, the polypeptides of the present invention are:

$H_2N$-Trp-His-Ser-Asp-Met-Glu-Trp-Trp-Tyr-Leu-Leu-Gly-COOH (F56) SEG ID NO: 1;

$H_2N$-Trp-His-Val-Asp-Glu-Thr-Trp-Trp-Leu-Leu-Met-Leu-COOH (F87) SEQ ID NO: 2;

$H_2N$-Trp-His-Asp-Pro-Thr-Pro-Trp-Trp-Ser-Trp-Glu-Ile-COOH (F90). SEQ ID NO: 3.

In another preferred embodiment, the polypeptide of the present invention is a fusion protein composed of an-amino acid sequence of formula (I) and another polypeptide. Based on the activities of the peptides of the present invention, it can be envisaged that peptides of the present invention can be fused with other functional peptides or proteins to form multifunctional fusion proteins of different forms. For example, it is possible to fuse the peptides of the present invention with the following peptides or proteins to form fusion proteins:

1. Various cytokines, such as interleukin-2, to topically activate T lymphocytes etc. while blocking the receptors in the tumor site;
2. Soluble receptor KDR or Flt-1, to exhibit double functions of blocking the receptor and binding VEGF by the soluble receptor, therefore to inhibit the binding of VEGF to its receptors by different ways at the same time;
3. Specific antibodies or fragments thereof such as tumor vascular endothelial cell specific antibody or fragment thereof, to make the in vivo distribution of the peptides of the present invention specific to a target;
4. Other functional peptides optionally through a linker of certain length, such as peptides for blocking receptor KDR disclosed in Chinese patent application 01142203.3 to the present inventor with the same filing date as the present application, in particular:

$H_2N$-His-Thr-Met-Tyr-Tyr-His-His-Tyr-Gln-His-His-Leu-COOH (K237) (SEQ ID NO: 4), $H_2N$-Met-His-Asn-His-His-Asn-His-Pro-Arg-Pro-Ser-Ser-COOH (K112) (SEQ ID NO: 5), or $H_2N$-Cys-Asp-Pro-Leu-Leu-Lys-His-His-Thr-His-Pro-Lys-COOH (K212) (SEQ ID NO: 6).

In this case, one molecule can block two kinds of receptors, KDR and Flt-1, therefore inhibit the binding of VEGF to its receptors more effectively;

5. B7 molecule, etc., to activate lymphocytes in the tumor tissue topically while blocking the receptors;
6. Any other peptides or proteins compatible with and functionally complementing or synergizing the peptides of the present invention.

In another preferable embodiment, the polypeptides of the present invention contain two or more amino acid sequences of formula (I), being identical or different, optionally with a suitable linker between the adjacent amino acid sequences. In other words, the peptides of the present invention can be connected with one another optionally through suitable linker(s) to form homo-multimers or hetero-multimers.

As used herein, "amino protective group" refers to a chemical group protecting an amino group of an amino acid or peptide from a reaction. For amino protective groups, see the description in Greene "Protective Groups In Organic Synthesis" (John Wiley & Sons, New York(1981)). For example, the amino protective groups include $C_1$-$C_6$-acyl such as acetyl group, propionyl group, pivaloyl group, tert-butyl acetyl group, etc.; other acyl such as 2-chloroacetyl group, 2-bromoacetyl group, trifluoro-acetyl group, trichloroacetyl, phthalyl group, benzoyl, 4-chloro-benzoyl, 4-bromo-benzoyl, 4-nitro-benzoyl, etc.; sulfonyl such as benzene-sulfonyl, para-tosyl, etc.; the groups capable of forming carbamate, such as carbobenzoxy group, para-chloro-carbobenzoxy group, para-methoxy-carbobenzoxy group, para-nitro-carbobenzoxy group, para-bromo-carbobenzoxy group, 3,4-dimethoxy-carbobenzoxy group, 3,5-dimethoxy-carbobenzoxy group, 2,4-dimethoxy-carbobenzoxy group, 4-methoxy-carbobenzoxy group, 2-nitro-4,5-dimethoxy-carbobenzoxy group, 3,4,5-trimethoxy-carbobenzoxy group, 1-(biphenylyl)-1-methyl ethoxycarbonyl group, α,α-dimethyl 3,5-dimethoxy carbobenzoxy group, diphenylmethoxycarbonyl group, t-butoxycarbonyl, diisopropyl methoxycarbonyl group, isopropoxy-carbonyl group, ethoxycarbonyl group, methoxycarbonyl group, allyloxycarbonyl group, 2,2,2-trichloroethoxycarbonyl group, phenoxycarbonyl group, 4-nitrophenoxycarbonyl group, flourenyl-9-methoxycarbonyl group, cyclopentyloxy-carbonyl group, adamantyloxycarbonyl group, cyclohexyloxy-carbonyl group, phenylthiocarbonyl group; aralkyl group such as benzyl, trityl, carbobenzoxy group, 9-flourenyl-methoxycarbonyl group (Fmoc), etc.; and silyl such as trimethylsilyl, etc. The preferred amino protective groups are formyl group, acetyl group, benzoyl group, pivaloyl group, tert-butyl acetyl group, benzenesulfonyl group, benzyl, tert-butoxycarbonyl group (Boc), carbobenzoxygroup (Cbz). For example, the α amino group of lysine is protected by an acid-labile group (such as Boc), while the ϵ amino group is protected by an alkali-labile group (such as Fmoc) so that a selective de-protection is possible in synthesis.

As used herein, a "carboxy protective group" refers to an ester or amido group protecting a carboxy group while functional group(s) on other site(s) is/are under reaction. For carboxy protective groups, see the description in Greene "Protective Groups In Organic Synthesis" (John Wiley & Sons, New York (1981)). For example, the carboxy protective groups include $C_1$-$C_8$ lower alky such as methyl, ethyl, tert-butyl, etc.; aralkyl groups such as phenethyl, benzyl, or substituted benzyl; aryl alkenyl such as phenylvinyl; dialkylaminoalkyl such as dimethylaminoethyl, etc. alkanoyloxyalkyl such as acetoxymethyl, butyroxymethyl, valeryloxymethyl, isobutyroxymethyl, isovaleryloxymethyl, 1-(propionyloxy)-1-ethyl, 1-(pivaloyloxy)-1-ethyl, 1-methyl-1-(propionyloxy)-1-ethyl, pivaloyloxymethyl, propionyloxymethyl, etc.; cycloalkanoyloxyalkyl such as cyclopropylcarbonyloxymethyl, cyclobutylcarbonyloxymethyl, cyclopentylcarbonyloxymethyl, cyclohexylcarbonyloxymethyl, etc.; arylcarbonyloxyalkyl such as benzoyloxymethyl, benzoyloxyethyl, etc.; araklycarbonyloxyalkyl such as benzylcarbonyloxymethyl, 2-2-benzylcarbonyloxyethyl, etc.; alkyoxycarbonylalkyl or cycloalkyoxycarbonylalkyl such as methoxycarbonylmethyl, cyclohexyloxycarbonylmethyl, 1-methoxycarbonyl-1-ethyl, etc.; alkyoxycarbonyloxyalkyl or cycloalkyoxycarbonyloxyalkyl such as methoxycarbonyloxymethyl, tert-butoxycarbonyloxymethyl, 1-ethoxycarbonyloxy-1-ethyl, 1-cyclohexyloxycarbonyloxy-1-ethyl, etc; aryloxycarbonyloxyalkyl such as 2-(phenoxycarbonyloxy)ethyl, 2-(5-indanyloxycarbonyloxy)ethyl, etc.; alkyoxyalkylcarbonyloxyalkyl such as 2-(1-methoxy-2-methyl-2-propionyloxy)ethyl, etc.; arylalkyoxycarbonyloxyalkyl such as 2-(benzyloxycarbonyloxy)ethyl, etc.; arylalkenoxycarbonyloxyalkyl such as 2-(3-phenylpropen-2-yl oxycarbonyloxy) ethyl, etc.; alkyoxycarbonylaminoalkyl such as tert-butyoxycarbonylaminomethyl, etc.; alkylaminocarbonylaminoalkyl such as methylaminocarbonylaminomethyl, etc.; alkanoylaminoalkyl such as acetaminomethyl, etc.; heterocyclylcarbonyloxyalkyl such as 4-methylpiperazinylcarbonyloxymethyl, etc.; dialkylaminocarbonylalkyl such as dimethylaminocarbonylmethyl, diethylaminocarbonylmethyl, etc. The preferred carboxy protective groups are $C_1$-$C_6$ lower alkyl, $C_3$-$C_7$ cycloalkyl or aralkyl ester, such as methyl ester, ethyl ester, propyl ester, isopropyl ester, butyl ester, sec-butyl ester, isobutyl ester, pentyl ester, isopentyl ester, cyclohexyl ester, phenethyl ester, etc.; or alkanoyloxycarbonyl, cycloalkanoyloxycarbonyl, arylcarbonyloxyalkyl or aralkylcarbonyloxyalkyl ester. For example, the α carboxy group of aspartate is protected by acid-labile group (such as tert-butyl), while the β carboxy group is protected by hydrogenation-labile group (such as benzyl) so that a selective de-protection is possible in the process of synthesis.

The naturally occurring amino acids (termed "genetically encoded") as used herein include polar amino acids: serine (Ser), threonine (Thr), cysteine (Cys), tyrosine (Tyr), aspartate (Asp), asparagine (Asn), glutamate (Glu), glutamine (Gln), lysine (Lys), arginine (Arg) and histidine (His); hydrophobic amino acids: glycine (Gly), alanine (Ala), valine (Val), leucine (Leu), isoleucine (Ile), proline (Pro), phenylalanine (Phe), tryptophan (Try) and methionine (Met). Unless otherwise indicated, the stereochemistry of the α carbon in said amino acids and the amino acid residues of peptides of the present inVention is the their natuial configuration, i.e., "L" configuration. Of course, this does not apply to a non-chiral amino acid.

Said amino acids of the present invention may have non-natural side chain residues, as in homo-phenylalanine, phenyiglycine, norvaline, norleucine, ornithine, thiazolyl alanine, etc.

The peptides of the present invention can be synthesized by conventional methods of solid phase peptide synthesis known to those skilled in the art. For example, the peptides of the present invention can be synthesized by solid phase chemistry techniques according to the procedures described by Steward and Young (Steward, J. M. and Young, J. D., Solid Phase Peptide Synthesis, 2nd Ed., Pierce Chemical Company, Rockford, Ill., (1984)) using an Applied Biosystem synthesizer or a Pioneer™ peptide synthesizer. Alternatively, multiple fragments may be synthesized then linked together to form larger fragments. For solid phase peptide synthesis, many related techniques are disclosed in Steward, J. M. and Young, J. D., Solid Phase Peptide Synthesis, W. H. Freeman Co. (San Francisco), 1963; and J. Meienhofer, Hormonal Proteins and Peptides, vol. 2, p.46, Academic Press (New York), 1973. Generally, these methods include sequential addition of one or more amino acids or suitably protected amino acids to a growing peptide chain. Normally, either the amino group or the carboxy group of the first amino acid is protected by a suitable protective group. Then the protected amino acid is attached to an inert support of solid phase, the next amino acid of the sequence with a suitably protected complementary amino group or carboxy group is added under the conditions suitable for forming the amide linkage. Then, the protective group is removed from the newly added amino acid residue, and the next amino acid that is suitably protected if required is added. The process is repeated until all the desired amino acids are linked in proper sequence. Any remaining protective groups and any solid support are removed sequentially or concurrently to give the final polypeptide. More than one amino acid can be added to the growing peptide chain at a time by simple modification to the above general procedure.

A particularly preferred method for preparing the peptides of the present invention involves solid phase peptide synthesis wherein the amino acid α amino group is protected by an acid or base sensitive protective group. The protective groups should be stable under conditions of forming peptide linkage but easy to remove without destructing the growing peptide chain and racemizing any of the chiral center contained therein. Suitable protective groups include 9-flourenyl methoxycarbonyl group (Fmoc), tert-butoxycarbonyl group (Boc), carbobenzoxy group (Cbz), 2-cyano-tert-butoxycarbonyl group, etc. 9-flourenyl methoxycarbonyl group (Fmoc) is particularly preferred for synthesizing the peptides of the present invention.

Other preferred side chain protective groups are 2,2,5,7,8-pentamethylchroman-6-sulfonyl (pmc), nitro, p-tosyl, 4-methoxybenzene-sulfonyl, Cbz, Boc and adamantyloxycarbonyl for side chain amino group of lysine and arginine; benzyl, o-bromo-carbobenzoxy group, 2,6-dichlorobenzyl, isopropyl, tert-butyl, cyclohexyl, cyclopentyl and acetyl for tyrosine; tert-butyl, benzyl and tetrahydropyranyl for serine; trityl, benzyl, Cbz, p-tosyl and 2,4-dinitrophenyl for histamine; formyl for tryptophan; benzyl and tert-butyl for aspartate and glutamate; trityl for cysteine.

In the method of solid phase peptide synthesis, first of all, the C-terminal α amino acid has to be attached to a suitable solid support or resin. The solid supports for the above-mentioned method are those materials that are inert to the reagents and reaction conditions of the stepwise condensation-deprotection reactions and insoluble in the solvents used. The preferred solid support for synthesis of α C-terminal carboxyl peptides is 4-hydroxymethylphenoxy-copoly (styrene-1% divinylbenzene). The preferred support of solid phase for synthesis of α C-terminal amide peptides is 4-(2',4'-dimethoxyphenyl-Fomc-aminomethyl)phenoxyacetamidoethyl resin available from Applied Biosystems (Foster City, Calif.). Generally, the C-terminal α amino acid is coupled to the resin according to the following method: the α amino acid is coupled with the resin for about 1 to 24 hours at 10 to 50° C. in appropriate solvent such as dichloromethane or DMF by means of N,N'-dicyclohexylcarbodiimide (DCC), N,N'-diisopropylcarbodiimide (DIC) or O-benzotriazole-1-yl-N,N,N',N'-tetramethyluronium hexafluorophosphate (HBTU), with or without 4-dimethylaminopyridine (DMAP), 1-hydroxybenzotriazole (HOBT), benzotriazole-1-yloxy-tri(dimethylamino)phosphonium hexafluorophosphate (BOP) or di-(2-oxo-3-oxazolidinyl) phosphine chloride (BOPCI). When the solid support is 4-(2',4'-dimethoxyphenyl-Fomc-aminomethyl)phenoxyl acetamidoethyl resin, the Fmoc group should be removed by a secondary amine (preferably piperidine) before coupling the C-terminal α amino acid according to the above-mentioned procedure. The preferred method for coupling with the deprotected 4-(2',4'-dimethoxyphenyl-Fomc-aminomethyl)phenoxy acetamidoethyl resin is to use O-benzotriazole-1-yl-N,N,N',N'-tetramethyluronium hexafluorophosphate (HBTU, 1 equivalent) and 1-hydroxybenzotriazole (HOBT, 1 equivalent) in DMF.

The subsequent coupling of amino acids can be performed in an automatic peptide synthesizer well known in the art. In a preferred embodiment, the α N-terminal amino acids of the growing peptide chain is protected by Fmoc. Protective group Fmoc can be removed from α N-terminal side of the growing peptide chain by a secondary amine (preferably piperidine). Each protected amino acid is added in about 3-fold molar excess. The coupling reaction is preferably performed in DMF. Generally the coupling agents are O-benzotriazole-1-yl-N,N,N',N'-tetramethyluronium hexafluorophosphate (HBTU, 1 equivalent) and 1-hydroxybenzotriazole (HOBT, 1 equivalent). At the end of the solid phase synthesis, the peptide is removed from the resin and deprotected, either successively or concurrently. The resin-polypeptide complex can be treated with a cleavage reagent containing thianisole, water, ethanedithiol and trifluoroacetic acid to carry out the removal of polypeptide and the deprotection simultaneously. The polypeptide may be removed from the resin by aminolysis with an alkylamine, if the α C-terminal of the polypeptide is an alkylamide. Alternatively, the polypeptide can be removed by transesterification (e.g., with methanol) followed by aminolysis or by direct transamidation. The protected polypeptide so cleaved can be purified or applied in the next step without purification. The protective groups of side chain can be removed by cleavage mixture set forth above. The fully deprotected polypeptide can be purified by using some or all types of the following chromatographic methods: ion exchange on a weakly basic resin (for example acetate form); hydrophobic adsorption chromatography on an underivitized poly(styrene-divinylbenzene) resin (for example Amberlite XAD); silica gel adsorption chromatography; ion exchange chromatography on carboxymethylcellulose; partition chromatography, e.g., on Sephadex G-25, LH-20, or countercurrent distribution; high performance liquid chromatography (HPLC), especially reverse-phase HPLC on a column of octyl- or octadecyl silica. The molecular weight of synthesized polypeptides may be determined by fast atom bombardment (FAB) mass spectrum. For the specific synthesis of the polypeptides of the present invention, see examples 1 to 3.

Long polypeptides and fusion proteins of the present invention are preferably obtained by expression of a polynucleotide containing the coding sequence of the polypeptide or fusion protein of the present invention in a suitable host and purification of the so-expressed polypeptide. Both sense and antisense DNA strands of the nucleotide sequences encoding the peptides of the present invention can be synthesized by phosphite triester method well known in the art on a DNA synthesizer. The oligonucleotides encoding the peptides of the present invention may be obtained by annealing the synthesized complementary sense and antisense DNA strands in a suitable buffer solution. In this synthesis process, cohesive terminal sequences for cloning purpose can be introduced to both ends of the oligonucleotide. Then the oligonucleotide encoding the peptide of the invention is linked by T4 ligase to a suitable vector containing the sequence encoding another polypeptide or protein digested by relevant restriction endonuclease to obtain the DNA sequence encoding the fusion protein. Generally, the coding sequence for another polypeptide or protein is known. Some of them can be obtained from the market in the form of vectors, others can be synthesized or cloned from a known organism based on conventional methods. The sequencing of the obtained gene sequence of the present invention or various DNA fragments can be performed by a conventional method such as dideoxy chain-termination method (Sanger et al., PNAS, 1977, 74: 5463-5467). The sequencing can also be performed by using commercial DNA sequencing kits. Of course, the expression vector should contain an appropriate promoter, ribosome binding site, terminator and the like. An appropriate leader sequence can be linked to the upstream of the polypeptide-coding sequence in order to direct the expressed product to certain cell apartments. The selection of an appropriate vector and promoter is well known to an ordinary person skilled in the art. An effective vector for bacteria can be constructed as follows: the structural DNA sequence encoding the target protein together with an appropriate initiation signal and termination signal for translation is inserted into an operable open reading frame containing a functional promoter. The methods for constructing a vector containing a nucleotide sequence of the present invention and appropriate regulatory elements for transcription and translation are well known to an ordinary person skilled in the art. It is known to those skilled in the art that, to express the target protein, an appropriate host should be selected according to the type of the expression vector or construct into which the DNA sequence of the present invention has been inserted. The appropriate hosts for the expression of the polypeptides of the present invention include, but not limited to, prokaryotic host such as *E. coli, Bacillus, Streptomyces* etc.; eucaryotic host such as *Saccharomyces* spp., *Aspergillus* spp.; insect cell such as *Drosophila* S2 cell and *Spodoptera frugiperda* Sf9; mammalian cells such as CHO and COS (monkey renal fibroblast cell line, Gluzman (Cell 23:175, 1981)); other cell lines capable of expressing a compatible vector. The methods for introducing a construct into the above-mentioned host cells are well known to those skilled in the art, and include, but not limited to, calcium chloride-mediated transformation, calcium phosphate-mediated transfection, DEAE-dextran-mediated transfection, electroporation, micro-injection, particle bombardment method or gene gun method (Sambrook, J. (1989), Molecular Cloning, a Laboratory Manual, Cold Spring Harbor Press; Plainview, N.Y.; Ausubel, F. M. (1989) Current Protocols in Molecular Biology, John Wiley & Sons, N.Y.; Hobbs, S. et al., McGraw Hill Yearbook of Science and Technology (1992), McGraw Hill, N.Y. 191-196; Engelhard, E. K. et al., PNAS, 91:3224-3227; Logan, J. et al., PNAS, 81:3655-3659). The transformed host strains or cells are cultured in a suitable culture medium under suitable culture conditions. When they grow to appropriate cell density, the selected promoter may be induced by an appropriate method (such as temperature transition or chemical induction). After the induction, the cells are cultured for another period of time. The selection of culture conditions and media corresponding to different host strains or cells and the features of the expressed target protein is within the knowledge of those skilled in the art. The expressed polypeptides or fusion proteins may be separated and purified from the culture by a conventional method such as centrifugation, precipitation, various chromatographies, HPLC, etc. Example 4 shows the cloning and expression process of a fusion protein which is composed of a peptide of the present invention and dihydrofolate reductase.

The peptides of the present invention have anti-angiogenesis activity. As shown in the experimental examples, the peptides can competitively inhibit the binding of VEGF to its receptor Flt-1, specifically inhibit the proliferation of angioendothelial cell, the proliferation of chick chorioallantoic membrane blood vessels, and the tumor growth and metastasis in nude mice. As angiogenesis inhibitor, the peptides of the present invention are useful for the treatment of primary or metastatic solid tumors and cancers of the following organs: breast, colon, rectum, lung, oropharynx, hypopharynx, esophagus, stomach, pancreas, liver, bilecyst, bile duct, small intestine; urinary system including kidney, bladder and epithelium of urinary tract; female genital system including unerine neck, uterus, ovary, chorioma and gestational trophoblastic diseases; male genital system including prostata, seminal vesicle and testis; endocrine glands including thyroid gland, adrenal gland and pituitary body; skin cancer including angioma, melanoma, sarcoma originated from bone or soft tissue, and Kaposi's sarcoma; tumors of brain, nervus, eye and meninges, including astrocytoma, neuroastrocytoma, spongioblastoma, retinoblastoma, neuroma, neuroblastoma, neurinoma and neuroblastoma; solid tumors developed from malignant diseases of hemopoietic system, including chloroleukemia, plasmacytoma and dermal T lymphoma/leukaemia; lymphoma including Hodgkin's lymphoma and non-Hodgkin's lymphoma. The peptides of the present invention can also be used to prevent autoimmune diseases, including rheumatoid arthritis, immune arthritis and degenerative arthritis; eye diseases, including diabetic retinopathy, Terry's syndrome, rejection of corneal implantation, retrolental fibroplasia, neovascular glaucoma, neovascularization of retina induced by degeneration of macula and anoxia; dermatosis including psoriasis; angiopathy including hemangioma and capillary proliferation in arteriosclerosis plaques; angiogenesis in cardiac muscle; neovascularization of plaques; capillarectasia; hemorrhagic articular angiofibroma; granulation of wound; diseases characterized in excessive or abnormal stimulation of endothelial cell, including regional ileitis of intestinal adhesion, arteriosclerosis, dermatasclerosis and hypertrophic scar; and other diseases associated with angiogenesis including ulcer. Additionally, the peptides of the present invention can inhibit ovulation and formation of placenta, therefore may be used as procreation-controlling agents. Peptides of the present invention can also be used in preventing metastasis of the above-mentioned tumors.

The compounds of the present invention can be used in the form of pharmaceutically acceptable salts. A "pharmaceutically acceptable salt" refers to salt without undue toxicity, stimulation, allergy etc. while contacting human or animal tissues. Pharmaceutically acceptable salts are well known in the art. The salts can be prepared during the final separation and purification process of the peptides of the present invention. The salts can also be prepared through the reaction of free base or acid form with suitable organic or inorganic acid or base. The representative acid addition salts include, but not limited to, acetate, adipate, alginate, citrate, aspartate, benzoate, benzenesulfonate, bisulfate, butyrate, camphorate, camphorsulfonate, glycerophosphate, semisulfate, heptylate, hexoate, fumarate, hydrochlorate, hydrobromate, hydriodate, 2-hydroxyethyl-sulfonate, lactate, maleate, methane-sulfonate, nicotinate, 2-naphthalene-sulfonate, oxalate, 3-phenyl-propionate, propionate, succinate, tartrate, phosphate, glutamate, bicarbonate, p-toluenesulfonate and undecylate. The preferred acids for forming pharmaceutically acceptable salts are hydrochloric acid, hydrobromic acid, sulfuric acid, phosphoric acid, oxatic acid, maleic acid, succinic acid and citric acid. The basic ions of pharmaceutically acceptable base addition salts include, but not limited to, alkali metal ions or alkaline earth metal ions such as lithium, sodium, potassium, calcium, magnesium and aluminum etc., and non-toxic quaternary ammonium such as ammonium, tetramethyl ammonium, tetraethyl ammonium, methylamine, dimethylamine, trimethylamine, triethylamine, diethylamine, ethylamine, diethylamide, ethanolamine, diethanolamine, piperidine and piperazine etc. The preferred base addition salts include phosphate, tris and acetate.

A pharmaceutical composition can be formulated by combining a peptide or a fusion protein of the present invention and a pharmaceutically acceptable excipient or carrier. Pharmaceutically acceptable carriers or excipients refer to nontoxic fillers, diluents, encapsulation materials or other adjuvants in the state of solid, semisolid or liquid. The pharmaceutical compositions can be administered via parenteral, sublingual, intracisternal, intravaginal, intraperitoneal, intrarectal, intrabuccal, intra-tumor or topical routes.

The parenteral administration includes intravenous, intramuscular, intraperitoneal, intrasternal, subcutaneous, intra-articular injection and transfusion. The pharmaceutical compositions suitable for parenteral administration include sterilized aqueous solution or non-aqueous solution, dispersion, suspension or emulsion, and powder to be dissolved in injectable sterile solution or dispersion liquid immediately before use. Suitable aqueous carriers or non-aqueous carriers, diluents, solvents or excipients include water, ethanol, glycerin, propylene glycol, polyethylene glycol, carboxymethyl cellulose, vegetable oil and injectable organic ester such as ethyl oleate. These compositions may also comprise adjuvants such as preservative, moisture agent, emulsifier and disperser etc. The addition of isotonic agent such as saccharide, sodium chloride may be advantageous.

The topical administration includes administrations on the surface of skin, mucosa, lung and eye. The pharmaceutical compositions for topical administration include powder, ointment, drops, transdermal patch, iontophoresis apparatus and inhalant etc. In the inhalational compositions, the peptides of the present invention are compressed or contained in a pressured gas propellant such as nitrogen or liquidized gas propellant. The peptides of the present invention are preferably not soluble in the liquidized propellant medium.

Preferably, the formulations for intrarectal or intravaginal administration are suppository that can be formulated through mixing the peptides of the present invention with appropriate non-stimulating excipients or carriers such as cacao butter, polyethylene glycol or suppository wax. Said excipients or carriers are solid at room temperature, but liquid at body temperature, therefore can be melted in the cavity of rectum or vagina releasing the active ingredients therein.

For administration by the above-mentioned routes or other routes, the therapeutically effective amount of peptides of the present invention can be in the pure form or the form of pharmaceutically acceptable salts with or without a pharmaceutically acceptable excipient. The term "therapeutically effective amount" refers to an amount of the peptides of the present invention sufficient to exhibit a therapeutic effect on the angiogenic diseases within a suitable therapeutic window. The specific therapeutically effective amount for a specific subject depends upon many factors including the nature and severity of the disease to be treated; the activity of the specific compound used; the specific composition used; the subject's age, body weight, gender, diet and general health status; administering time; administering route; the excretion rate of the specific compound; duration of treatment; other drugs administered jointly or simultaneously. For example, the total daily dose of a peptide of the present invention may be 0.05-20 mg/kg body weight when administered topically, 0.15-50 mg/kg body weight when administered systemically. The daily dose of a fusion protein having a molecular weight of 27,000 dalton may be 0.05-60 mg/kg body weight when administered topically, 0.5-150 mg/kg body weight when administered systemically. The daily dose can be divided and administered for several times in one day if necessary. Therefore, the single dosage form of the compositions can comprise the total daily dose or part of the same.

In another aspect, the present invention also relates to polynucleotides encoding the polypeptides of the present invention as defined above.

The present invention also relates to gene therapy. That is, the therapeutic effects are obtained through transferring the gene encoding a polypeptide of the present invention into a subject's cells to express the polypeptide in vivo. A variety of the methods for transferring or delivering DNA to cells for expressing proteins are known in the art, for example in N. Yang, "In Vivo Gene Transfer in Mammal Somatocytes", Crit. Rev. Biotechn. 12(4): 335-356(1992). Gene therapy includes incorporation of DNA sequences into somatocytes or germ cells for ex vivo or in vivo therapy.

There are three main types of methods of gene transfer for gene therapy: (1) physical methods, such as electroporation, direct gene transfer and particle bombardment, (2) chemical methods, such as methods lipid-based vectors and other non-viral vectors, and (3) biological methods, such as viral vectors. For example, a non-viral vector such as liposome containing DNA can be intravenously injected to a subject. Alternatively, vectors or "naked" DNA gene can be injected into the target organ, tissue or tumor directly to deliver the therapeutic DNA to the target.

The basic methods of gene transfer include ex vivo gene transfer, in vivo gene transfer and in vitro gene transfer. For ex vivo gene transfer, the cells are obtained from a specific subject and cultured in a cell medium. Then a DNA is transfected into the cells. The transfected cells are expanded and are re-transplanted into the same subject. For in vitro gene transfer, the cells to be transformed are the cells cultured in a medium such as cultured tissue cells instead of specific cells from a specific subject. These "Laboratory Cells" are transfected. The transfected cells are selected and cultured to proliferate, and then transplanted into a subject or used for other purposes. In vivo gene transfer involves DNA transfer into the cells which maintain in the body of a subject.

The biological gene therapy is preferred in the present invention, that is, the gene is inserted into cells by means of a viral vector. As used herein, the term "vector" refers to a vector which contains or binds with a certain polynucleotide sequences, and is responsible for delivering these polynucleotide sequences into the cells. The cells to be transfected can be obtained from a normal tissue or a focus tissue of a subject or not from a specific subject. The examples of vectors include plasmid, infectious microbe like virus, or non-viral vectors such as ligand-DNA conjugate, liposome and lipid-DNA complex.

A recombined DNA molecule containing the DNA sequence encoding the peptide or fusion protein of the present invention is effectively linked to a regulatory sequence to form an expression vector which can express the polypeptides or the fusion proteins of the present invention. The viral vectors which have been used in gene therapy include, but not limited to, retrovirus, other RNA virus such as poliomyelitis virus or sindbis virus, adenovirus, adeno-associated virus, herpes virus, simian virus 40, poxvirus or other DNA virus. Murine replication defective retrovirus vector is the most popular vector for gene transfer. Viral vectors have also been used to insert gene into cells in vivo. To express a heterogenous gene in target tissue specifically, a known tissue-specific cis-regulatory element or promoter can be used. Alternatively, DNA in situ delivery or anatomical site-specific viral vectors can also be used to achieve the same effect. For example, the gene transfer to vessels has been achieved by transplantation of endothelial cells from a chosen site of the artery wall which are transfected in vitro. Surrounding cells infected by the virus can also express the gene products. Alternatively, viral vectors can be delivered to a site in vivo directly (for example through catheter), thereby only a few sites are infected by the virus and long-term site-specific gene expression is provided. In vivo gene transfer in mammary tissue and hepatic tissue has been achieved using retrovirus vectors wherein the recombined virus is injected to the vessels directing to these organs.

Accordingly, the present invention further relates to a plasmid or viral vector containing a polynucleotide of the present invention, and a cell containing a polynucleotide or vector of the present invention.

As mentioned above, the present invention relates to a polynucleotide encoding a polypeptide of the present invention, vector or cell containing the polynucleotide used as gene therapeutical medicament.

Correspondingly, the present invention relates to a pharmaceutical composition for treating angiogenic diseases. The composition comprises a polynucleotide, vector or cell of the present invention, and a pharmaceutically acceptable excipient, especially one suitable for gene therapy if required.

Based on the use of a polynucleotides of the present invention in gene therapy, the present invention relates to use of a polynucleotide or vector as defined above for the preparation, from cells obtained from a subject, of cells to be re-transplanted to the subject for treating angiogenic diseases.

Finally, the present invention relates to a method for treating angiogenic diseases comprising administering to a subject in need such treatment a therapeutically effective amount of a peptide, polynucleotide, vector or cell as defined in the present invention.

The present invention is further illustrated by the following examples which however are not intended by any way to restrict the protection scope of the present invention.

EXAMPLE 1

$H_2$N-Trp-His-Ser-Asp-Met-Glu-Trp-Trp-Tyr-Leu-Leu-Gly-COOH (F56) (SEQ ID NO: 1).

Peptide synthesis column packed with 4-(2',4'-dimethoxyphenyl-Fomc-aminomethyl)phenoxylacetamidoethyl resin was loaded in a Pioneer™ peptide synthesizer. The peptide was synthesized in nitrogen according to the following steps:

1. The resin was solvated in DMF for 5 minutes;
2. The resin was treated with 20% piperidine in DMF for 15 minutes to remove the protective group Fmoc on the grafted group of the resin (or on α-amino group of the amino acid attached to the resin);
3. The resin was rinsed by DMF for several minutes;
4. The α-carboxy group of the first amino acid Gly (Fmoc-Gly) of C terminal was activated with 0.2 M solution of HBTU and HOBT in DMSO-NMP (N-methyl-pyrrolidone) and 0.4 M diisopropylethylamine solution;
5. The activated amino acid obtained in step 4 was coupled with the resin of step 2 (or the amino acid attached to the resin) in DMF for about 30 minutes;
6. The resin was rinsed by DMF for 5 minutes;
7. Steps 2-6 were repeated with the following amino acids:

Fmoc-Leu→Fmoc-Leu→Fmoc-Tyr(tBu)→Fmoc-Trp→Fmoc-Trp→Fmoc-Glu(γ-OtBu)→Fmoc-Met→Fmoc-Asp(β-OtBu)→Fmoc-Ser(tBu)→Fmoc-His(Trt)→Fmoc-Trp;

8. The resin was rinsed with THF for about 5 minutes;
9. The resin and a fresh cleavage mixture (thianisole: water ehtanedithiol:trifluoroacetic acid=2:1:1:36, by volume) were mixed and stirred for 10-15 minutes at 0° C., and then stirred for 2 hours at room temperature;
10. The reaction mixture was filtrated and the filtrate was centrifuged in cold ethyl ether. The supernatant was poured out and centrifuged in cold ethyl ether again until the peptide was fully precipitated. The raw peptide was purified by chromatography on a preparative C18 silica gel column. The column was eluted gradiently by acetonitrile/(water, 0.1% TFA). The fractions containing the target peptide were collected and lyophilized to obtain 30 mg of the title peptide.

EXAMPLE 2

$H_2$N-Trp-His-Val-Asp-Glu-Thr-Trp-Trp-Leu-Leu-Met-Leu-COOH (F87) (SEQ ID No: 2).

The title peptide was prepared according to the procedure described in Example 1. The first amino acid was Fomc-Leu. The following amino acids were added according to the following order under said conditions: Fmoc-Met→Fmoc-Leu→Fmoc-Leu→Fmoc-Trp→Fmoc-Trp→Fmoc-Thr(tBu)→Fmoc-Glu(γ-OtBu)→Fmoc-Asp(β-OtBu)→Fmoc-Val→Fmoc-His(Trt)→Fmoc-Trp. 35 mg of the title peptide was obtained.

EXAMPLE 3

$H_2$N-Trp-His-Asp-Pro-Thr-Pro-Trp-Trp-Ser-Trp-Glu-Ile-COOH (F90) (SEQ ID NO: 2).

The title peptide was prepared according to the procedure described in Example 1. The first amino acid was Fomc-Lle. The following amino acids were added according to the following order under said conditions: Fmoc-Glu(γ-OtBu)→Fmoc-Trp→Fmoc-Ser(tBu)→Fmoc-Trp→Fmoc-Trp→Fmoc-Pro→Fmoc-Thr(tBu)→Fmoc-Pro→Fmoc-Asp(β-OtBu)→Fmoc-His(Trt)→Fmoc-Trp. 44 mg of the title peptide was obtained.

EXAMPLE 4

Preparation of Fusion Protein
DHFR-F56/DHFR-F90

1. Preparation of the DNA Encoding Peptides

According to a DNA sequence encoding peptide F56 or F90, sense and antisense single strand DNA fragments were synthesized on a DNA synthesizer (ABI, 318A type) by the solid phase phosphite triester method. Cohesive terminal sequences for cloning were added to both ends of the single strand DNA fragments. 30 ng of each of sense and antisense DNA were incubated in 8 μl TE in water bath at 65° C. for 5 minutes, and cooled down to room temperature in 15-30 minutes gradually.

2. Construction of DHFR-F56/DHFR-F90 Expression Vector and Induced Expression on Small Scale The expression plasmid for dihydrofolate reductase, pQE 42, was digested by Pst I and Hind III (purchased from New England Biolabs) in turn and retrieved by Qick kit (product of QIAGEN company). The purified vector fragment was linked to the annealed oligonucleotide fragment obtained according to the above 1) by $T_4$ DNA ligase (purchased from New England Biolabs). Due to the anti-ampicillin activity of E. coli M15, 1 μl linkage product was transferred into JM109 by electroporation first, and the positive clones were selected by LB (1.5% agar, 100 μg/ml ampicillin) medium. Then the plasmids were amplified and identified by BamH I digestion. The method of the identification and the principle thereof are as follows: each of the DNA sequences of F56, F90 has a digestion site of BamH I. There is also a digestion site of BamH I on the vector DNA fragment close to the Pst I site. Therefore, a DNA band of about 700 bp can be obtained through digestion of the constructed pQE 42-F56/F90 by BamH I, but not from the same digestion of the empty vector without cloning fragment inserted in. The results of the identification by digestion were totally coincident with the principle, indicating that F56 and F90 have been cloned into the expression vector pQE42.

The right plasmid pQE42-F56/F90 identified by digestion was transformed into *E. coli* M15. The transformed products were screened by being spread on LB culture dishes (1.5% agar, 100 μg/ml ampicillin, 25 μg/ml kanamycin). The positive clones were selected and cultured in LB (100 μg/ml ampicillin, 25 μg/ml kanamycin), and protein expression was induced by IPTG (0.1 mmol/L). The expressed products were analyzed by 10% SDS-PAGE.

3. Large Scale Expression and Purification of DHFR-F56/DHFR-F90 Fusion Protein

The bacteria pellet from 100 ml culture broth of large scale induced expression was suspended in 2 ml TE solution and incubated in ice bath. The bacteria were lysed by intermittent ultrasound for 30 s and centrifuged (12,000g, 10 minutes, 4° C.). The supernatant was discarded. The pellet was suspended in 2 ml sodium deoxycholate (20 g/L) by ultrasound and incubated at room temperature for 30 minutes. The suspension was centrifuged (10,000 g, 10 minutes, 4° C.) to obtain the inclusion body as pellet. A certain volume of denaturing solution was added to the inclusion body and incubated at room temperature for 3 hours. Then, 10× volume of renaturing solution was added slowly. After the solution was incubated at room temperature for 3-4 hours, its pH value was adjusted to 8. The solution then was centrifuged (10,000 g, 4° C., 10 minutes). The purity and content of the protein was analyzed by 10% SDS-PAGE.

4. Western Blot Assay

Protein DHFR (positive control), DHFR-F56, DHFR-F90 and 6His-Kringle (I-V) (negative control) were loaded onto 10% SDS-PAGE to perform electrophoresis. Murine monoclonal antibody specific for DHFR prepared by the inventor's laboratory was used as the primary antibody. Horseradish peroxidase labeled rabbit-anti-mouse antibody was used as the secondary antibody. The binding of DHFR specific monoclonal antibody to DHFR, DHFR-F56, DHFR-F90, 6-His-Kringle (I-V) were analyzed by Western blot. The analysis results of the fusion proteins obtained in the present example were positive.

EXMAPLE 5

Binding of DHFR-F56/DHFR-F90 to sFlt-1 and Endothelial Cell

The specificity of the binding of the fusion proteins DHFR-F56 and DHFR-F90 to receptor Flt-1 was tested by ELISA in the present example.

Particularly, a 96-well plate was coated with soluble receptors, sFlt-1, sKDR (5 mg/L, 50 μl/well) [Song Shumei, Shou Chengchao: Molecular cloning and its expression of vascular endothelia growth factor receptor KDR. Chin J. Biochem. Mol. Bio. 1998, 14 (1): 57-61; An Ping, Dong Zhewei and Shou Chengchao: Molecular cloning and its bio-activity of soluble VEGF receptor expressed in bacterial. Chin J. Biochem. Mol. Bio. 2000, 16 (1): 62-66]. Alternatively, the vascular endothelial cells in a 96-well plate were fixed by pre-cooled 0.125% glutaraldehyde solution. DHFR, DHFR-F56 or DHFR-F90 was added to the plate after blocking. An ELISA assay was carried out using a DHFR-specific monoclonal antibody according to conventional method. The ELISA assay was repeated for 3 times.

The results are shown in the following table 1. The results show that DHFR-F56 and DHFR-F90 can bind to Flt-1 and endothelial cells, and have no notable reaction with KDR. The negative control, DHFR, has no reaction with sFlt-1, KDR or endothelial cells. These results indicate that the binding of DHFR-F56/DHFR-F90 to sFlt-1 and endothelial cells is specific.

TABLE 1

Test for the specificity of the binding of DHFR-F56/DHFR-F90 by ELISA ($OD_{492}$ nm)

|  | DHFR-F56 | DHFR-F90 | DHFR |
|---|---|---|---|
| SFlt-1 | 0.529 | 0.415 | 0.088 |
| SKDR | 0.081 | 0.074 | 0.074 |
| EC | 0.477 | 0.384 | 0.080 |

EXAMPLE 6

Inhibition of the Binding of VEGF to Receptor Flt-1 by DHFR-F56

In order to detect the activity of DHFR-F56 blocking VEGF binding to sFlt-1, a binding assay was carried out using $^{125}$I-VEGF (purchased from Life Technology Inc.).

The experiment was carried out according to a method substantially as described by Tanaka, K., et al (Characterization of the extracellular domain in vascular endothelial growth factor receptor-1 (Flt-1 tyrosine kinase). Jpn J Cancer Res. 1997, 88:867-876). Briefly, a 96-well plate was coated overnight at 4° C. by 0.5 mg/L soluble receptor of VEGF, Flt-1 (sFlt-1). The coating solution was 0.01 mol/L phosphate buffer (pH 6.2). Then, the plate was rinsed with a washing solution (0.9% NaCl, 0.01 mol/L, pH6.2) for 3 times. 250 μl blocking buffer (0.3% BSA, 25 mmol/L HEPES, DMEM, pH7.6) was added into each well for 3 hours at room temperature. DHFR-F56 of different concentrations (1, 5, 10, 15, 20 μg/ml) (DHFR of different concentrations for the control group) and $^{125}$I-VEGF (purchased from Life Technology Inc.) of fixed concentration (2 μg/L, 50 μg/well) were added to the wells. 2 parallel wells were used for each concentration. The binding reaction underwent for 1 hour at room temperature. The plate was rinsed 4 times with the binding buffer. After the 96-well plate was dried completely, a liquid-scintillation solution was added into the plate (120 μl/well). The cpm value was determined by a Wallac co liquid-scintillation counter after the solid residue had been dissolved.

Figure 1:
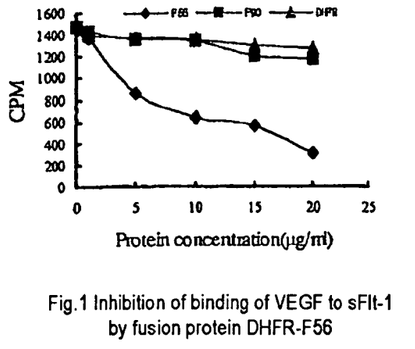
FIG. 1. Results of a radio-immunological competitive inhibition test for determining the inhibition of the binding of VEGF to the soluble receptor, sFlt-1, by fusion proteins containing different peptides of the present invention.

The results are shown in FIG. 1. The binding of $^{125}$I-VEGF to coated sFlt-1 decreases along with the increase of the concentration of DHFR-F56, while the, change of the concentration of DHFR has no notable effect on the binding of $^{125}$I-VEGF to sFlt-1. There is statistically significant difference between DHFR-F56 group and DHFR group (hypothesis testing of paired data comparison, t test, α=0.05). This indicates that F56 can competitively inhibit the binding of VEGF to receptor Flt-1.

17

EXAMPLE 7

Effect of Peptide F56/F90 to the Proliferation of Endothelial Cells

A sample of human umbilical cord (obtained from Beijing Gynecological and Obstetric Hospital) was digested by 0.1% collagenase II (purchased from GIBCO BRL Corporation), and centrifuged at 1000 rpm for 10 minutes to collect the human umbilical cord vein-derived endothelial cells (HUVECs). The cells were suspended in 20% FCS/RPMI 1640 (purchased from GIBCO BRL Corporation), and transferred to a plastic culture flask and cultured in a incubator (37° C., 5% $CO_2$) for 2 days. Then, the cultured HUVECs were digested with 0.04% trypsin-EDTA, and inoculated into a 24-well plate at $3 \times 10^4$ cells/well. After 24 hours' incubation, the cells were incubated for another 24 hours in new medium 2% FCS/RPIM 1640. $VEGF_{165}$ (product of Sigma Corporation) was added either independently or as a mixture with peptide F56 or F90 of different concentrations (50, 100, 200, 300 μmol/L). 4 parallel wells were used for each group. The cells were incubated for 48 hours. Then, $^3$H-TdR(1 μci/ml) was added and the cells were incubated for another 8 hours. The cells were collected to a glass-fiber filter membrane. The cpm value was detected according to conventional methods. The same experiment was repeated for 3 times.

Figure 2:
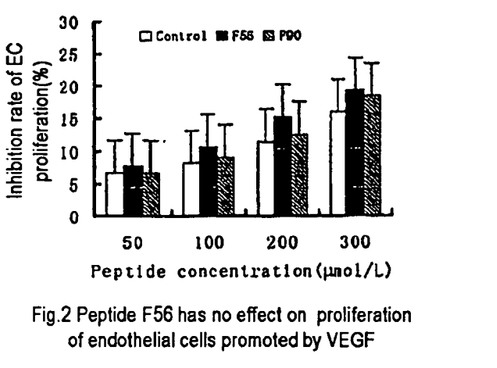
FIG. 2. Results of an experiment for determining the inhibition of the VEGF-stimulated proliferation of human umbilical vein-derived endothelial cells by different peptides of the present invention.

The results are shown in FIG. 2. Peptide F56/F90 has no significant inhibition to the proliferation of umbilical cord vein-derived endothelial cells. This is consistent with the theory that the binding of VEGF to Flt-1 does not result in the proliferation of endothelial cells.

EXAMPLE 8

Inhibition of the Proliferation of Blood Vessels on Chick Chorioallantoic Membrane by F56

In this example, a proliferation assay on chick chorioallantoic membrane blood vessels was carried out to detect the inhibition of F56 to angiogenesis.

The experiment was carried out according to a method described by Fu Shengfa et al. (Fu Shengfa, Lu Yinglin and Zhang Chaoshan: Technique of detecting the effects of vascular growth factor with chorioallantoic membrane of fertilized chicken eggs. Chin Mili. Acad. Medi. Scie. 1993, 17:294-97"). Particularly, fresh inseminated chicken eggs were soaked in 0.1% benzalkonium bromide solution for 2 minutes at 38° C., and incubated in an incubator at 37.5° C., 60-70% humidity for 3 days. Then, the eggs were stripped and cultured on a petri dish. When the allantoic membrane grew to about $1cm^2$, the different groups (5 chick embryos per group) were treated with the following agents. $VEGF_{165}$ (2 μg/L), DHFR (negative control) or 18 μl F56 solution (0.8 μg/μl) was dropped onto a glass-fiber filter membrane (Φ5 mm). The membrane was placed on the distal end (in relation to the heart of the embryo) of the chorioallantoic membrane. The agents were administered once in the morning and once in the evening for 2 days. The results were observed and recorded by photography. The experiment was repeated twice (Kodak 100, exposed for 3 s).

Figure 3:
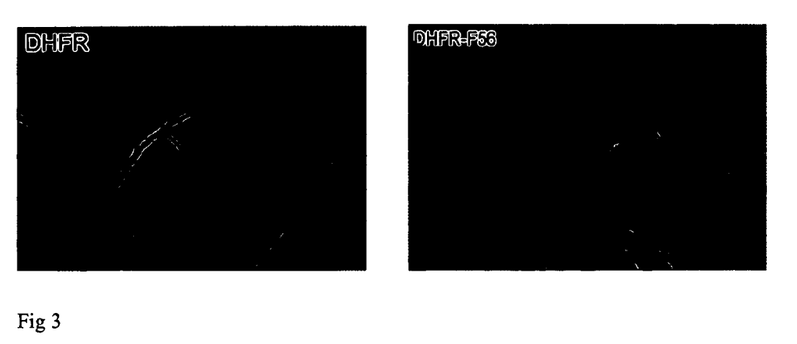
FIG. 3. Results of an experiment for determining the inhibition of the proliferation of blood vessels on chick chorioallantoic membrane by a peptide of the present invention: (A) VEGF stimulated the blood vessels to proliferate significantly; (B) DHFR had no notable effect on the blood vessels; (C) the blood vessels of chick embryo treated by F56 and F90 were derangeable in distribution and atrophic.

The results are shown in FIG. 3. The results indicate that human $VEGFI_{165}$ can promote the proliferation of chick chorioallantoic membrane blood vessels (FIG. 3A). While F56 can lead to the rupture of blood vessels and bleeding in addition to blood vessel atrophy (FIG. 3C). DHFR has no notable effect on the proliferation of chick chorioallantoic membrane blood vessels (FIG. 3B). This indicates that F56 has the biological activity of anti-angiogenesis.

18

EXAMPLE 9

Inhibition of Tumor Growth in Nude Nice by DHFR-F56/DHFR-F90

To testify whether DHFR-F56 and DHFR-F90 can inhibit tumor growth on the basis of anti-angiogenesis, a tumor inhibition test on Balb/c nude mice was performed.

MGC803 cells (a human gastric carcinoma cell line) was subcutaneously implanted on the right buttock of eight 5-week aged nude mice (purchased from the Animal Center of the Chinese Academy of Medical Sciences) ($2 \times 10^6$ cells/0.1 ml/each mouse). On the fifth day after the implantation, the nude mice were grouped at random into 2 groups each of which included 4 mice. DHFR (150 μg/100 μl per time), DHFR-F56 or DHFR-F90 (150 μg/100 μl per time) was injected intraperitoneally every other day for 10 times. The nude mice were observed for 30 days after withdrawal. The major and minor axes of the tumors were measured by vernier caliper every three days during the observation period. The volume of the tumor was calculated according to the formula of ½×major axis×minor $axis^2$. After the 30 days, the nude mice were put to dead by neck-breaking. The tumors were weighted and analyzed statistically.

Figure 4:
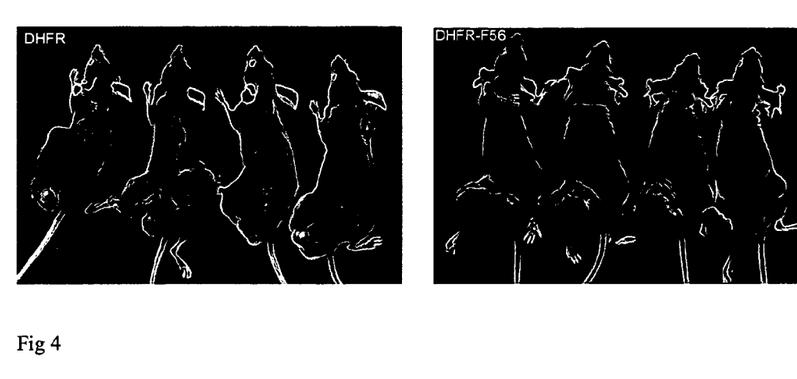
FIG. 4. Inhibition of the growth of tumor in nude mice by intraperitoneally injected fusion protein containing of a peptide of the present invention. It shows the state of tumor on the 30th day after withdrawal.
Figure 5:
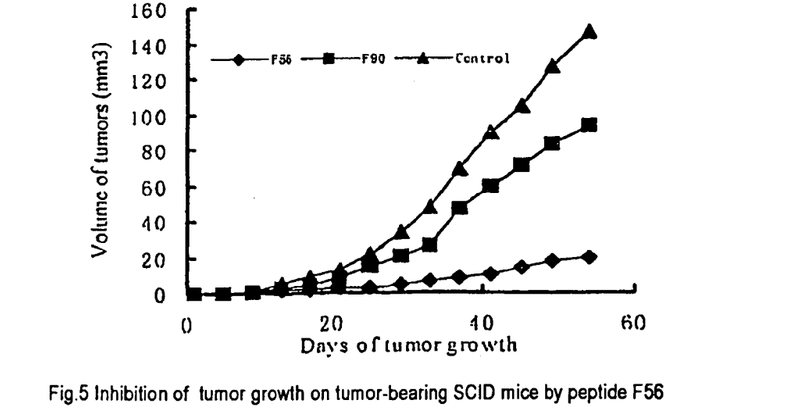
FIG. 5. Inhibition of the growth of tumor in nude mice by intraperitoneally injected fusion protein containing a peptide of the present invention. It shows the growth curve of tumor in nude mice after administrating.

The results are shown in FIG. 4 and FIG. 5. Both DHFR-F56 and DHFR-F90 can inhibit the growth of human gastric carcinoma MGC803 cells in Balb/c nude mice, and slow the growth rate of tumor. The statistical analysis (two-sample t test) indicates that the tumor volume of treatment group is smaller generally. There is significant difference between the treatment group and the DHFR control group ($p<0.05$). Furthermore, DHFR-F56 can also result in necrosis of tumor (FIG. 4).

EXAMPLE 10

Inhibition of Cancer Metastasis by F56

In order to observe the inhibitory activity of the peptides of the present invention to cancer metastasis, a metastasis model of breast cancer in SCID mice as described by Li Zhihong at al. (Transplant of human breast cancer in nude mice. Natl. Med J Chin. Vol.80 (11), 2000) was used to determine the function of F56. Briefly, human breast cancer cells were inoculated under the fat pad in the breast of SCID mice. Peptide F56 (0.5 mmol/L) was injected topically (60 μl per mouse per time) on the next day and every other day for 10 times in total. After 8 weeks, the mice were put to dead. The tumors were taken out and weighted. The whole lung was taken out, fixed and sliced with maximal cross-section and dyed by HE. The number of metastatic foci was counted. The results as shown in table 2 indicate that F56 can significantly inhibit cancer metastasis to lung in addition to the inhibition of tumor growth on the injection sites.

TABLE 2

F56 inhibited the metastasis of breast cancer cells to lungs of SCID mice

| Peptide | Number of metastatic foci in each mouse | | | | | Total number | Mean | Metastasis inhibition (%) |
|---|---|---|---|---|---|---|---|---|
| | 1 | 2 | 3 | 4 | 5 | | | |
| F56 | 0 | 0 | 1 | 2 | 2 | 5 | 1.0 | 70.5 |
| Solvent | 5 | 4 | 3 | 2 | 3 | 17 | 3.6 | 0 |

The invention claimed is:

1. A synthetic polypeptide having the amino acid sequence of SEQ ID NO.:1, and pharmaceutically acceptable salts thereof.

2. A fusion polypeptide comprising the polypeptide of claim 1 and dihydrofolate reductase.

3. A pharmaceutical composition comprising a polypeptide of claim 1 and a pharmaceutically acceptable carrier or excipient.

4. A method of treating disease marked by increased angiogenesis comprising administering to a subject with said disease a therapeutically effective amount of a polypeptide of claim 1.

* * * * *

SEQUENCE LISTING

<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: Antagonist Peptide

<400> SEQUENCE: 1

Trp His Ser Asp Met Glu Trp Trp Tyr Leu Leu Gly
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Antagonist Peptide

<400> SEQUENCE: 2

Trp His Val Asp Glu Thr Trp Trp Leu Leu Met Leu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Antagonist Peptide

<400> SEQUENCE: 3

Trp His Asp Pro Thr Pro Trp Trp Ser Trp Glu Ile
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Antagonist Peptide

<400> SEQUENCE: 4

His Thr Met Tyr Tyr His His Tyr Gln His His Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Antagonist Peptide

<400> SEQUENCE: 5

Met His Asn His His Asn His Pro Arg Pro Ser Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Antagonist Peptide

```
<400> SEQUENCE: 6

Cys Asp Pro Leu Leu Lys His His Thr His Pro Lys
1               5                   10
```